(12) United States Patent
McVean et al.

(10) Patent No.: US 9,427,274 B1
(45) Date of Patent: Aug. 30, 2016

(54) SURGICAL CUTTING SYSTEM AND METHOD

(71) Applicant: Z'egist Solutions, LLC, North Richland Hills, TX (US)

(72) Inventors: Dovie McVean, North Richland Hills, TX (US); Gary McVean, Durango, CA (US); James McVean, Durango, CO (US)

(73) Assignee: Z'egist Solutions, LLC, North Richland Hills, TX (US)

(*) Notice: Subject to any disclaimer, the term of this patent is extended or adjusted under 35 U.S.C. 154(b) by 210 days.

(21) Appl. No.: 14/056,676

(22) Filed: Oct. 17, 2013

(51) Int. Cl.
*A61B 17/88* (2006.01)

(52) U.S. Cl.
CPC .................................. *A61B 17/8863* (2013.01)

(58) Field of Classification Search
CPC ........................ A61B 17/8863; A61B 2017/90
See application file for complete search history.

(56) References Cited

U.S. PATENT DOCUMENTS

| | | | |
|---|---|---|---|
| 5,988,027 A | 11/1999 | Lenox | |
| 7,207,995 B1 | 4/2007 | Vandewalle | |
| 8,127,454 B1 | 3/2012 | Gao | |
| 2011/0107601 A1 | 5/2011 | Crainich et al. | |
| 2011/0253760 A1* | 10/2011 | McClintock et al. | ............ 225/2 |

FOREIGN PATENT DOCUMENTS

GB 2463522 3/2010

* cited by examiner

*Primary Examiner* — David Bates
*Assistant Examiner* — Olivia C Chang
(74) *Attorney, Agent, or Firm* — Elizabeth Philip Dahm; Kelly J. Kubasta; Ferguson, Braswell & Fraser, PC

(57) ABSTRACT

A surgical cutting system has a rod cutting tool and a guide device. The rod cutting tool includes a housing containing a drive motor and a cutting element mounted on the housing connected with the drive motor. The guide device includes a guide body, an attachment mechanism for attaching the rod cutting tool to the guide body, an elongate body movably mounted on the guide body, a rod-clamping element operably mounted on the elongate body, to lockingly engage the rod during the spinal fusion surgery and position the cutting element adjacent the rod. The cutting system also includes an adjustment mechanism for moving the elongate body relative to the guide body thereby moving the cutting element to cut the rod.

8 Claims, 13 Drawing Sheets

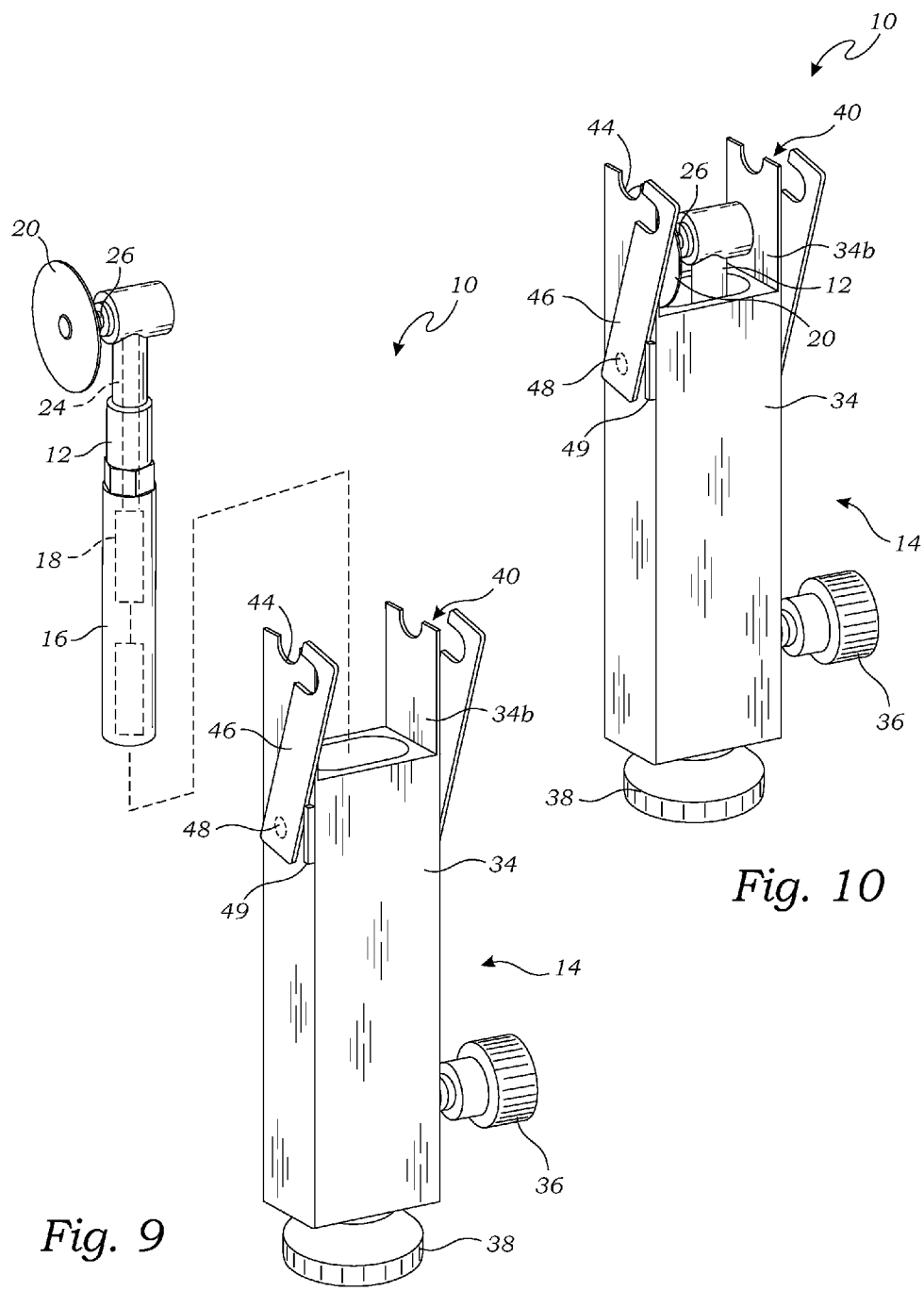

SURGICAL CUTTING SYSTEM AND METHOD

FIELD OF THE INVENTION

The present invention relates generally to rod cutting systems, and more particularly to surgical cutting system for cutting a rod used for spinal fixation in a patient's body.

BACKGROUND OF THE INVENTION

In a human body the spinal column encloses the spinal cord and consists of a number of bones (called vertebrae) superimposed upon one another in a series which provides a flexible supporting column for the trunk and head. There are normally thirty-three vertebrae in humans, including the five that are fused to form the sacrum and the four coccygeal bones that form the tailbone. The upper three regions comprise the remaining twenty-four, and are grouped under the names cervical (seven vertebrae), thoracic (twelve vertebrae) and lumbar (five vertebrae), according to the regions they occupy.

Spinal fusion is a surgical technique in which one or more of the vertebrae of the spine are united together so that motion no longer occurs between them. Spinal fusion is done most commonly in the lumbar region of the spine, but it is also used to treat cervical and thoracic problems. Patients requiring spinal fusion have either neurological deficits or severe pain which has not responded to conservative treatment. Spinal fusion surgeries are also common in patients who suffer from moderate to severe back deformities that require reconstructive surgery.

The basic principle of spinal fusion surgery involves adding bone graft to an area of the spine to set up a biological response that causes the bone graft to grow between the two vertebral elements and create a fusion, thereby stopping the motion at that segment. The bone graft can be taken from the patient's hip or harvested from cadaver bone or manufactured as a synthetic bone graft.

In most cases, the fusion is augmented by a process called fixation, meaning the placement of metallic screws (pedicle screws often made from titanium), rods or plates, or cages to stabilize the vertebra to facilitate bone fusion. The fusion process typically takes six to twelve months after surgery. During this time external bracing may be required.

The pedicle screw provides a means of gripping a spinal segment. The screws themselves do not fixate the spinal segment, but act as firm anchor points that can then be connected with a rod. The screws are placed at two or three or multiple consecutive spine segments (e.g. lumbar segment 4 and 5) and then a rod is used to connect the screws. This prevents the motion at the segments that are being fused. After the bone graft grows, the pedicle screws and rods are no longer needed for stability and may be safely removed with a subsequent back surgery. However, most surgeons do not recommend removal unless the pedicle screws cause discomfort for the patient.

Pedicle screws are connected by plates or rods that span single or multiple vertebral segments. Crossbars may be added for additional strength. For multilevel fusion involving more than two vertebrae, rods are generally preferred over plates because rods can be individually cut and molded as required to facilitate maintenance of the alignment. The tips of pedicle screws should be embedded in the vertebral bone and should not breach the anterior vertebral body cortex.

It is important that the rods are of precise lengths for the patient and the spanned vertebrae. Various rod cutters are known in the prior art, for example Rinner U.S. Pat. No. 6,058,820 discloses a rod cutter having two force-applying members pivotally attached together. The cutters both have extending ends which are pivotally connected together and have rod cutting edges thereon.

Similarly GB 2463522 discloses a controlled feed mechanism attachable to a power tool, such as a surgical power tool, controls the rate at which a cutting tool such as a reamer is fed into a work piece, irrespective of the axial force applied by an operator or surgeon, by pulling itself along a threaded guide rod inserted in the workpiece. Various types of cutting tools may be fitted, including those used in hip resurfacing surgery such as a single pass cutter which permits the barrel cut, chamfer cut and end cut required to resurface the head of a femur to be made in one pass.

U.S. Pat. No. 5,988,027 discloses a manually operated surgical steel rod cutter. The rod cutter has a rod shearing tool head for cutting a rod when the rod is provided within aligned bores of two shearing subassemblies of the tool head. To cut the rod, an operator rotates an extendable handle to a substantially vertical position, inserts the rod in the tool head and rotates the handle to a substantially horizontal position.

Similarly US 20110107601 discloses a rod cutter apparatus which includes a rod holding plate having a rod opening for receiving a rod to be cut, a cutting member having a central opening defined by a cutting edge, the central opening being substantially aligned with the rod opening; and a drive assembly connected between the rod holding plate and the cutting member to cause oscillation of the cutting member relative to the rod holding plate, wherein oscillation of the cutting member relative to the rod holding plate cuts a rod in the rod opening.

The prior art teaches rod cutting systems which are table mounted and are manually operable. The prior art also includes systems which involve cutting the rods by using powered cutters. Most of the systems used in prior art uses scissor like blades which are moved either manually of by power to cut the rod outside the patient's body and then use it in the surgery. However, the prior art does not teach a rod cutter which is power operated and can be used in the surgery area in very tightly controlled manner.

In view of the limitations inherent in the available rod cutting systems, there exists a need for an improved surgical cutting system, capable of overcoming disadvantages inherent in conventional surgical cutting systems in a fast, robust, cost effective, secure, and environmental friendly manner. The present invention fulfils this need and provides further advantages as described in the following summary.

SUMMARY OF THE INVENTION

In view of the prior art, the general purpose of the present invention is to provide an improved combination of convenience and utility, to include the advantages of the prior art, and to overcome the drawbacks inherent therein.

In one aspect, the present invention provides a surgical cutting system for cutting a rod as part of spinal fusion surgery. The surgical cutting system comprises a rod cutting tool and a guide device. The rod cutting tool includes a housing containing a drive motor and a cutting element mounted on the housing connected with the drive motor. The guide device includes a guide body, an attachment mechanism for attaching the rod cutting tool to the guide body, an elongate body movably mounted on the guide body, a rod-clamping element operably mounted on the elongate body to lockingly engage the rod during the spinal fusion surgery and position the cutting element adjacent the rod. The cutting system also includes an adjustment mechanism for moving the elongate body relative to the guide body thereby moving the cutting element to cut the rod.

A primary objective of the present invention is to provide a surgical cutting system for cutting a rod having advantages not taught by the prior art.

Another objective is to provide a surgical cutting system that may be used to cut the rod while it is implanted in a patient's spine.

A further objective is to provide a surgical cutting system that is easy to use, and which prevents accidental injury to the patient during use.

These together with other aspects of the invention, along with the various features of novelty that characterize the invention, are pointed out with particularity in the claims annexed hereto and forming a part of this disclosure. For a better understanding of the invention, its operating advantages and the specific objects attained by its uses, reference should be had to the accompanying drawings and descriptive matter in which there are illustrated exemplary embodiments of the invention.

BRIEF DESCRIPTION OF THE DRAWINGS

The advantages and features of the present invention will become better understood with reference to the following more detailed description taken in conjunction with the accompanying drawings in which:

FIG. 9 is a perspective view of the surgical cutting system, according to an alternative embodiment of the present invention;

FIG. 10 is a perspective view of the surgical cutting system, according to the embodiment shown in FIG. 9;

Like reference numerals refer to like parts throughout the several views of the drawings.

DETAILED DESCRIPTION

Figure 1:
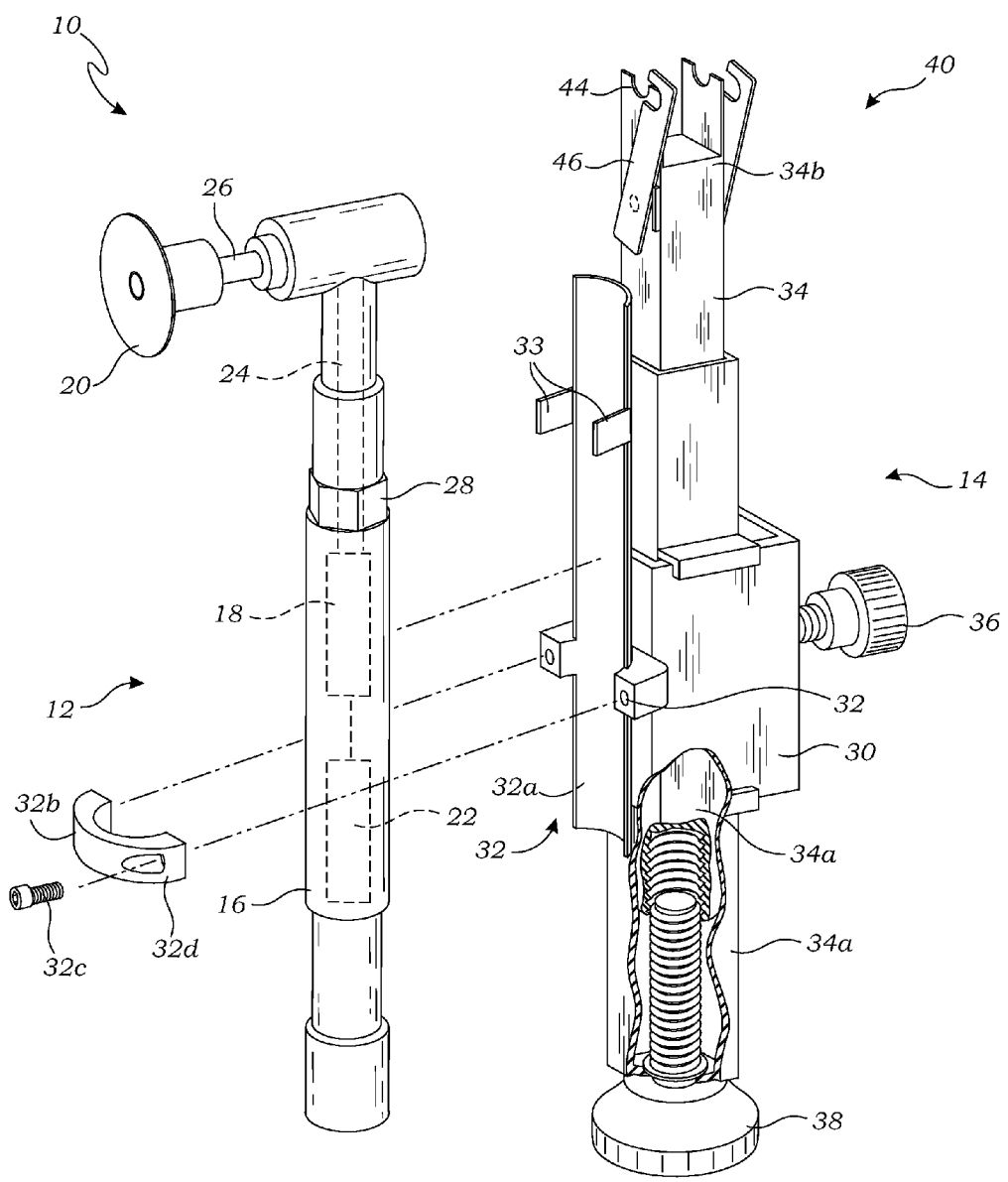
FIG. 1 is an exploded perspective view of a surgical cutting system.

FIG. 1 is an exploded perspective view of a surgical cutting system 10 according to one embodiment of the present invention. The surgical cutting system 10 is used for cutting a rod (shown in FIG. 2) as part of spinal fusion surgery, as discussed in greater detail below. The surgical cutting system 10 comprises a rod cutting tool 12 and a guide device 14 for guiding the rod cutting tool 12 for making a controlled cut of the rod.

In the present embodiment, the rod cutting tool 12 includes a housing 16 containing a drive motor 18 and a cutting element 20 operably mounted on the housing 16 and operably connected to the drive motor 18. The housing 16 further includes a power source 22 to provide power to the drive motor 18 and a transmission 24 to transfer the rotary motion from the drive motor 18 to the cutting element 20. In one embodiment the rod cutting tool 12 is a rotary cutting tool, and the cutting element 20 is a cutting disk, however in alternative embodiments the cutting element 20 may be a drill bit which would drill away the material of the rod, in effect cutting it. The cutting element 20 is supported on a cutting shaft 26 which is perpendicular to the axis of the housing 16. The cutting shaft 26 may be of any length such that when clamped, the position of the cutting element 20 along the rod is variable. The cutting element 20 rotates in a plane perpendicular to the axis of the rod to cut the rod along its length. The cutting element 20 may be made from any appropriate material that is well known within the art, such as hardened stainless steel or hardened tool steel or the like. The cutting element may be made of a material which is strong enough to cut the rods, which are typically made from titanium, cobalt, implantable plastic, or any other implantable material.

The power source 22 may be a rechargeable battery of sufficient strength to supply power to the drive motor 18. In an alternative embodiment, the power source 22 may include a power cord (not shown) for connecting the rod cutting tool 12 to a standard power socket. Any alternative power source may be used, according to the design of one skilled in the art, and such alternatives should be considered within the scope of the present invention.

The transmission 24 may include any form of belt, gear, chain or any suitable transmission mechanism to transfer the rotary motion of the drive motor 18 to the cutting element 20. The housing 16 is in the form of a hollow cylinder shaped to accommodate all the components of the rod cutting tool 12. The housing 16 may include facets 28 on the outer surface, which may be used to prevent rotation of the rod cutting tool 12 while in use, as described in greater detail below.

The rod cutting tool 12 may further include a control mechanism like an ON/OFF switch and/or a speed control switch for controlling the operation of the drive motor 18, which may be a hand held switch or foot pedal. In an alternative embodiment the housing 16 may be made into any other tubular cross section shape instead of circular as shown in FIG. 1. The different cross section shapes may include, but are not limited to, oval, hexagonal or any shape which serves the purpose of holding the components inside.

The rod cutting tool 12 may be independently used to cut the rod outside the patient's body. In the present invention, the rod cutting tool 12 is used after attaching it to the guide device 14, to enable a great deal of control and precise movement of the cutting element 20 for cutting inside the patient's body.

The guide device 14 includes a guide body 30, an attachment mechanism 32 for attaching the rod cutting tool 12 to the guide body 30, and a elongate body 34, in this embodiment an elongate body that extends from a proximal end 34*a* to a distal end 34*b*. The elongate body 34 is movably mounted on the guide body 30 for moving up and down between an extended position and a retracted position. In one embodiment, the guide body 30 is a tubular body that may have a generally rectangular cross section, or any other suitable cross-sectional shape. While one embodiment the elongate body 34 is the elongate body illustrated, in alternative embodiments the rod engaging body may be in another shape or configuration determined by one skilled in the art, that is effective for moving the guide body 30 as described for cutting the rod.

In this embodiment, the attachment mechanism 32 for attaching the rod cutting tool 12 to the guide body 30, may include a curved receiver element 32*a*, in this case a longitudinally cut hollow cylinder, that is shaped to receive the rod cutting tool 12. A C-clamp 32*b* fits around the rod cutting tool 12 for fastening the rod cutting tool 12 against the curved receiver element 32*a*. Fasteners 32*c* (e.g., screws) fit through the C-clamp 32*b* and engage apertures 32*d* for fastening the C-clamp 32*b* in place.

While one embodiment of the attachment mechanism 32 is illustrated, any equivalent fastening mechanism or system (e.g., straps, other forms of fasteners, screws, bolts, belts, buckles, etc.) may be used, and should be considered within the scope of the present invention.

The curved receiver element 32*a* may further include locking walls 33 positioned to lockingly engage the facets 28 of the rod cutting tool 12 to prevent movement of the cutting tool 12.

The guide body 30 may further include a lateral adjustment screw 36 which may be used to adjust the lateral position of the guide body 30 on the elongate body 34, as discussed in greater detail below.

The guide device 14 also includes a rod-clamping element 40 operably mounted on the distal end 34*b* of the elongate body 34. The rod-clamping element 40 is adapted to lockingly engage the rod during the spinal fusion surgery and position the cutting element 20 adjacent to the rod. This position of the elongate body 34 and guide body 30 is referred as the extended position of the elongate body 34.

The guide device 14 further includes an adjustment mechanism 38 for moving the elongate body 34 relative to the guide body 30 from the extended position to a retracted position in which the rod cutting element 20 cuts the rod. In one embodiment the adjustment mechanism 38 is a screw mechanism which is rotated to move the elongate body 34 relative to the guide body 30.

Also shown in FIG. 1 are two movable arms 46 which may be used to clamp the rod 42 to the surgical cutting system 10. In FIG. 1, a pair of movable arms 46 are shown, though in other embodiments there may only be one (as shown in all subsequent figures). The movable arms 46, and the clamping mechanism in general, are more fully described in the discussion of FIGS. 2-3, below.

Figures 2, 3:
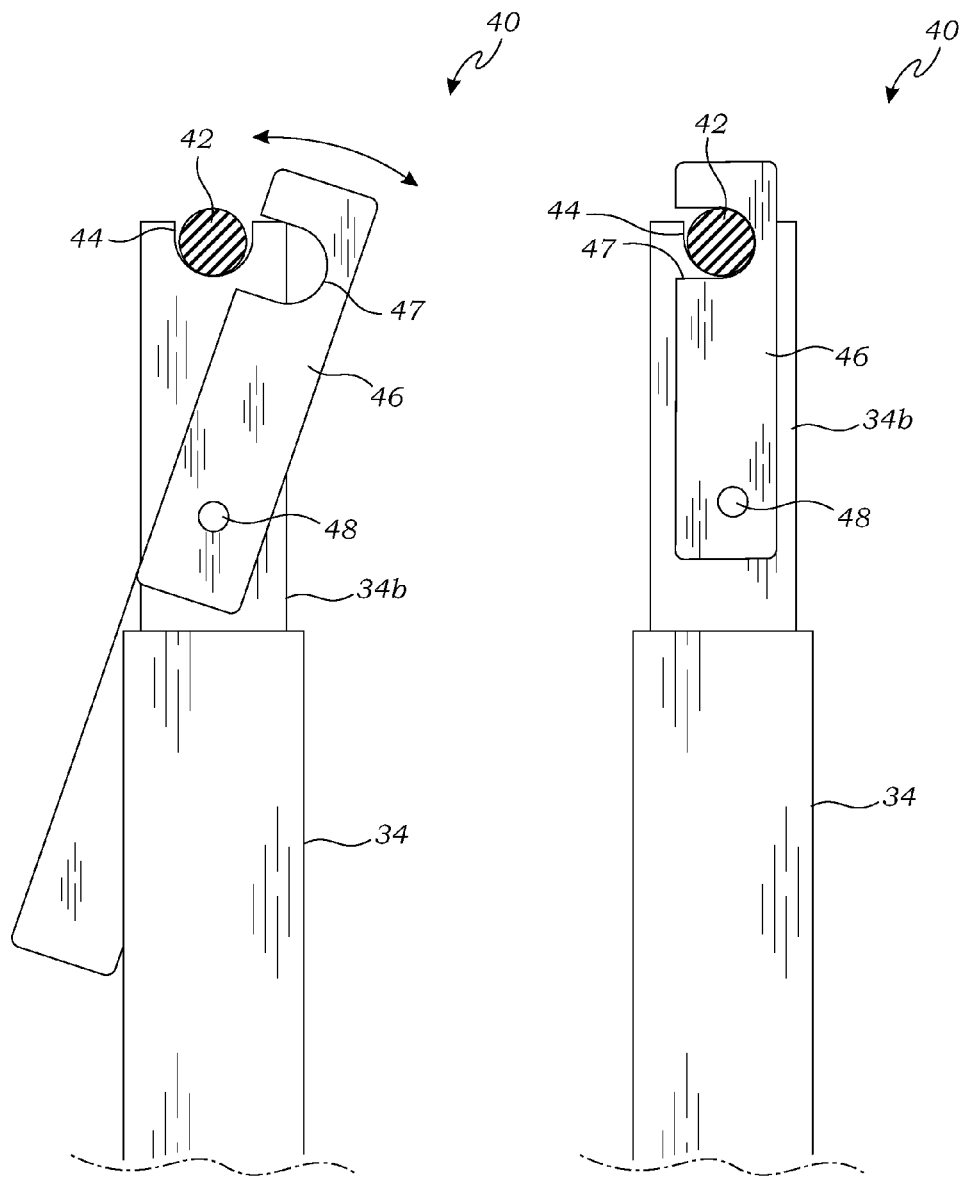
FIG. 2 is an elevation view which illustrates a rod-clamping element in an unlocked position.
FIG. 3 is an elevation view which illustrates the rod-clamping element in a locked position to lock a rod in place for cutting.

FIGS. 2 and 3 are elevation views which illustrate the rod-clamping element 40 in an unlocked position and a locked position respectively to receive a rod 42, according to one embodiment of the present invention. In one embodiment the rod-clamping element 40 may include a generally C-shaped receiver 44 in the terminal end of the elongate body 34, and the movable arm 46 that can move between a locked position and an unlocked position, and which includes a recessed portion 47 that fits around the rod 42 when the movable arm 46 is in the locked position and locks the rod 42 in the C-shaped receiver 44 of the elongate body 34. Also, the rod-clamping element 40 may be replaced with similar rod-clamping elements 40 that fit different sizes of rods 42, such replacement may be by snapping into place the replacement rod-clamping elements 40, or using other attachment methods known to those skilled in the art.

Each of the two C-shaped receivers 44 may include a pair of vertical strips with a C-shaped cut on its top edge, mounted on the elongate body 34. The movable arm 46 also includes a pair of vertical strips with the recessed portion 47, which is similar to the C-shaped cut on the receiver 44. The movable arm 46 can rotate about a pin 48 which engages it with the C-shaped receiver 44. As illustrated in FIG. 2 when the movable arm 46 is in open position the rod 42 can be placed in the C-shaped receiver 44. The movable arm 46 may be rotated along the direction shown by the curved arrow to bring the arm in locked position as shown in FIG. 3. When the rod 42 is locked, the rod cutting tool 12 may be used to cut the rod 42.

In one embodiment the rod-clamping element 40 may be mounted on the distal end 34*b* of the elongate body 34. In another embodiment the rod-clamping element 40 may be formed as an integral part of the elongate body 34 located at the distal end 34*b*. While one embodiment of the rod-clamping element 40 is illustrated herein, those skilled in the art may devise many alternative structures that function to suitably clamp the rod 42, and such alternative structures should be considered within the scope of the present invention.

Figure 4:
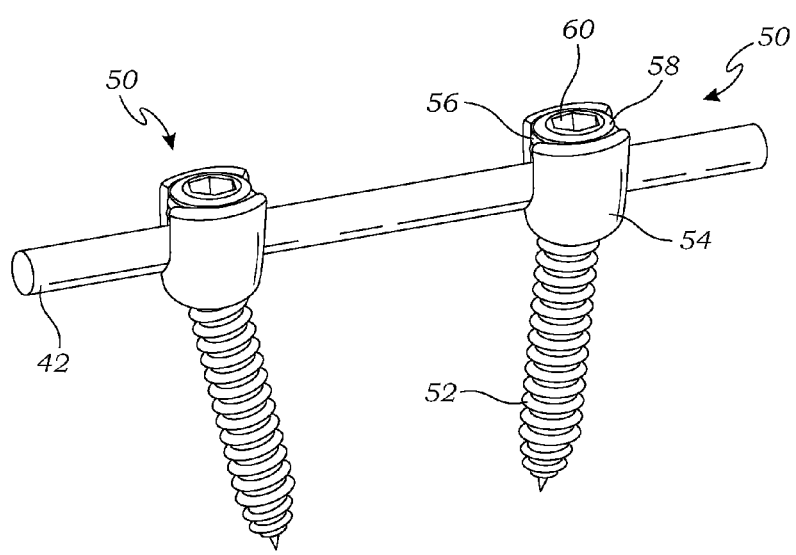
FIG. 4 is a perspective view of the rod positioned through two pedicle screws.

FIG. 4 is a perspective view of the rod 42 positioned through two pedicle screws 50. The pedicle screw 50 includes an elongate externally threaded portion 52 and a head 54. The head 54 is in the shape of a hollow cylinder open at the top and has a groove. The groove is used to receive the rod 42 on the head 54 of the pedicle screw 50. The head 54 has a threaded internal surface 56 which allows a locking nut 58 having external threads which corresponds with the internal thread of the head to be screwed into the head 54. The locking nut 58 further includes a driver receiver bore 60 which allows a screwdriver to be received and tighten the locking nut 58 when needed.

Figure 5:
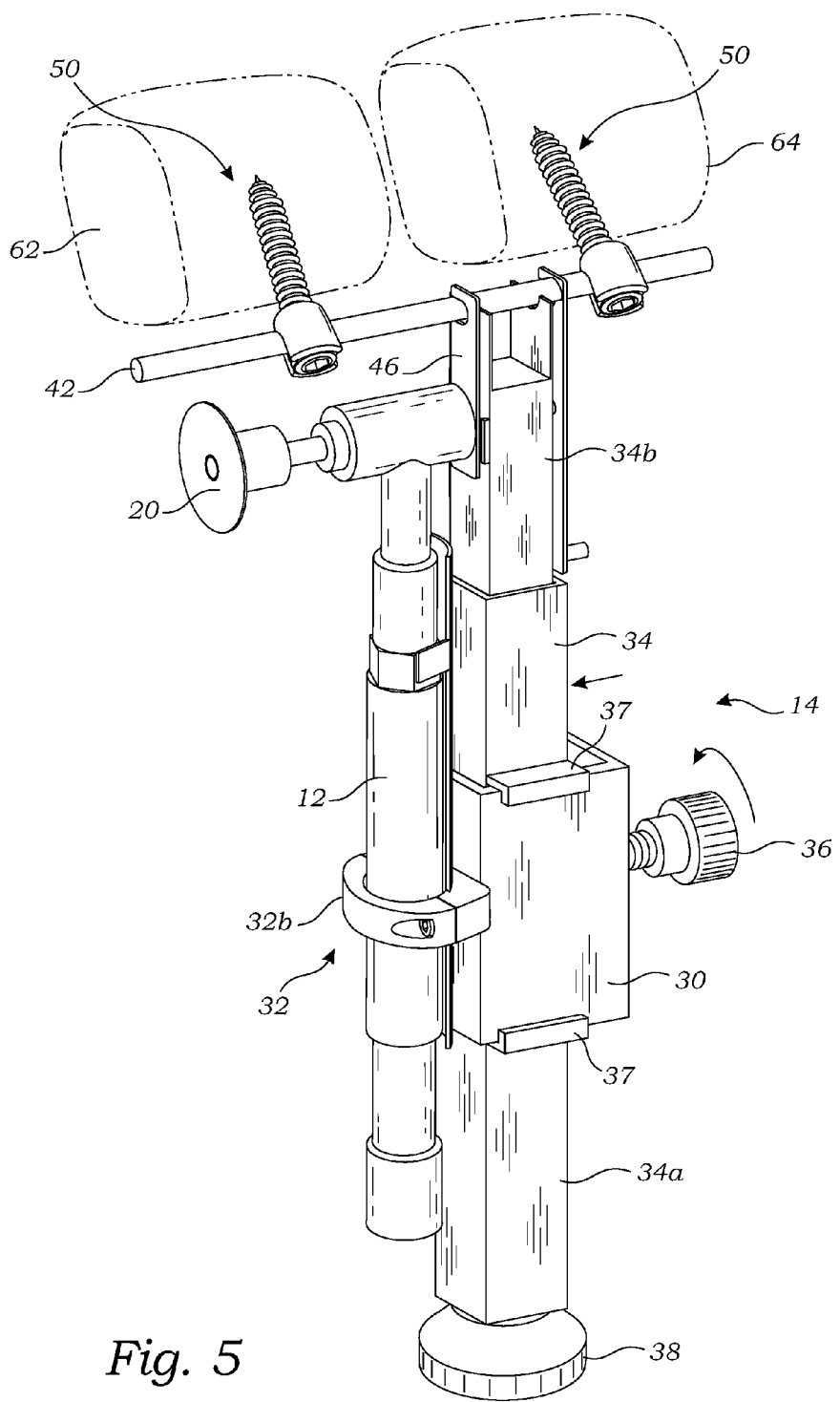
FIG. 5 is a perspective view of the surgical cutting system illustrating an elongate body in the extended position.
Figure 6:
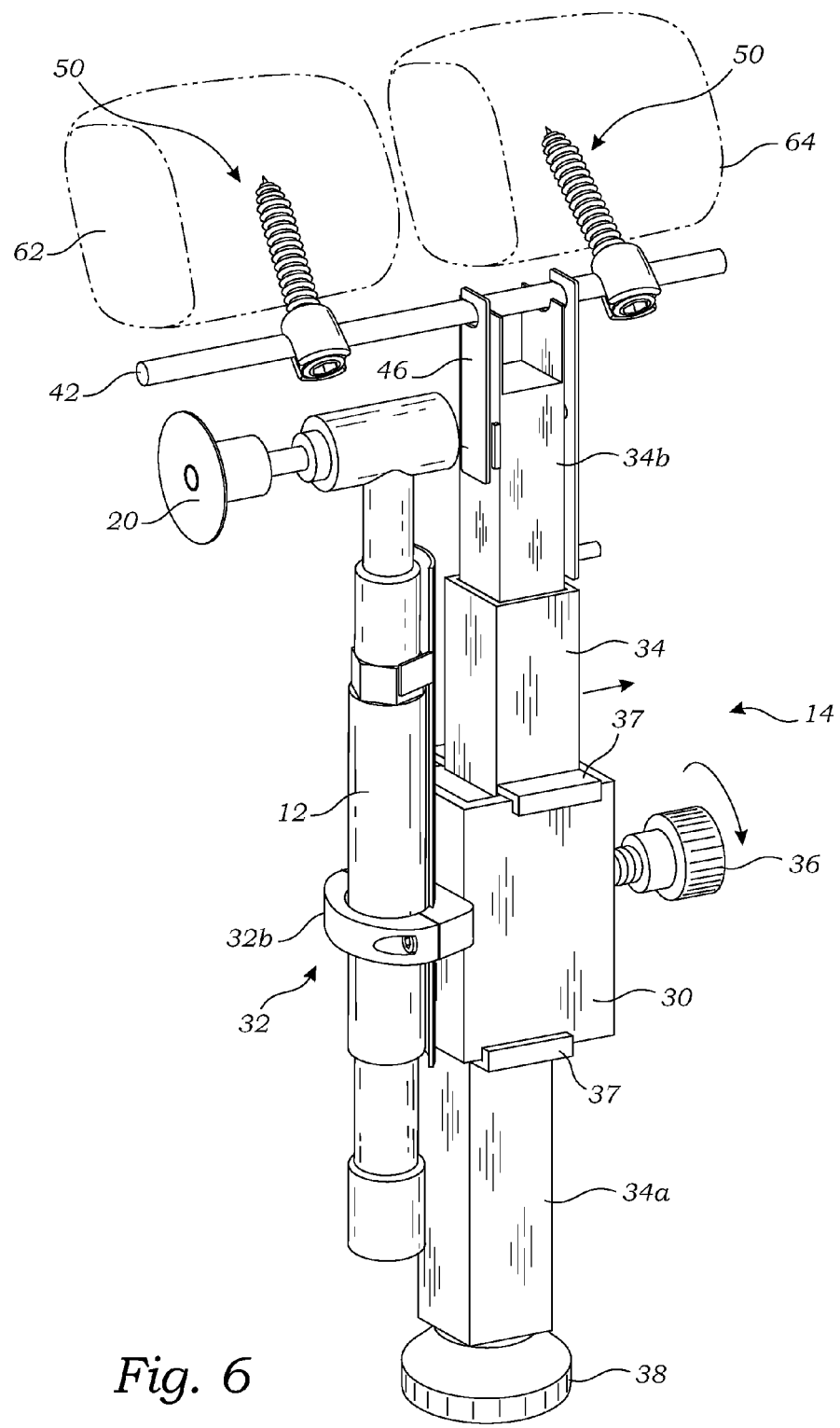
FIG. 6 is a perspective view of the surgical cutting system as shown in FIG. 5, having the elongate body in the retracted position.

FIG. 5 is a perspective view of the surgical cutting system 10 illustrating the elongate body 34 in the extended position, according to one embodiment of the present invention. FIG. 6 is a perspective view of the surgical cutting system 10 illustrating the elongate body in the retracted position, according to one element of the present invention. The pedicle screws 50 are positioned in two vertebrae 62, 64 of a patient with the rod 42 being positioned through the pedicle screws 50.

As illustrated in FIG. 5 and FIG. 6, the surgical cutting system 10 is assembled by attaching the rod cutting tool 12 with the guide body 30 using the attachment mechanism 32. The rod cutting tool 12 is attached such that the facets 28 are aligned with the locking walls 33 and the C-clamp 32*b* is tightened. The C-shaped receivers 44 are aligned to receive the rod 42 and the movable arm 46 is moved to lock the rod 42. The surgical cutting system 10 is operably mounted on the rod 42 with the elongate body 34 in the extended position such that the cutting element 20 is operably positioned adjacent the rod 42. At this point the drive motor 18 may be started to rotate the cutting element 20. Also, the distal end 34b will be able to accommodate the head of one of the pedicle screws 50 to help with stabilization of the surgical cutting system 10.

As illustrated in FIG. 5 and FIG. 6, the cutting system 10 may further include a lateral adjustment mechanism 36 for moving the rod cutting tool 12 laterally with respect to the rod 42, for adjusting the location of the cut on the rod 42. In this embodiment, the lateral adjustment mechanism 36 includes a lateral adjustment screw 36 which operates to move the elongate body 34 laterally with respect to the guide body 30, and thereby adjust the lateral position of the cutting tool 12 with respect to the rod 42. This enables the user to precisely position the cutting element 20 to cut the rod 42 at a desired location. In this embodiment, the cutting tool 12 is mounted on a frame 35 that is slidably mounted on rails 37. Turning the screw 36 causes the frame 35 to slide on the rails 37 thereby causing the lateral adjustment. While one embodiment of the lateral adjustment mechanism 36 is illustrated herein, alternative constructions known to those skilled in the art are also considered within the scope of the claimed invention.

Figure 7:
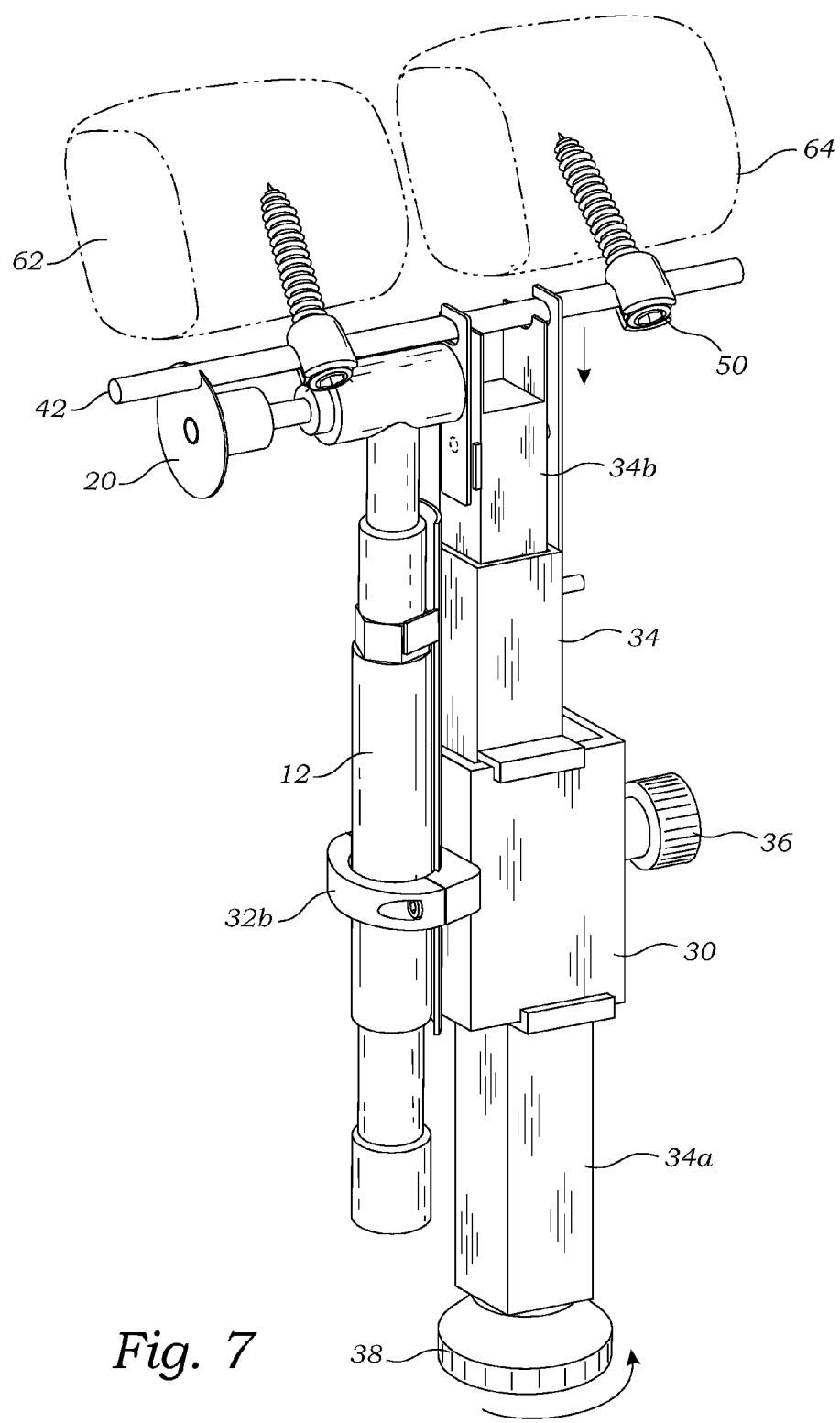
FIG. 7 is a perspective view of the surgical cutting system, illustrating the process of making a cut into the rod.

FIG. 7 is a perspective view of the surgical cutting system 10, illustrating the process of making a cut into the rod 42. This is done by turning the adjustment mechanism to retract the distal end 34b into the elongate body, thus bringing the rod 42 and cutting element 20 into contact.

Figure 8:
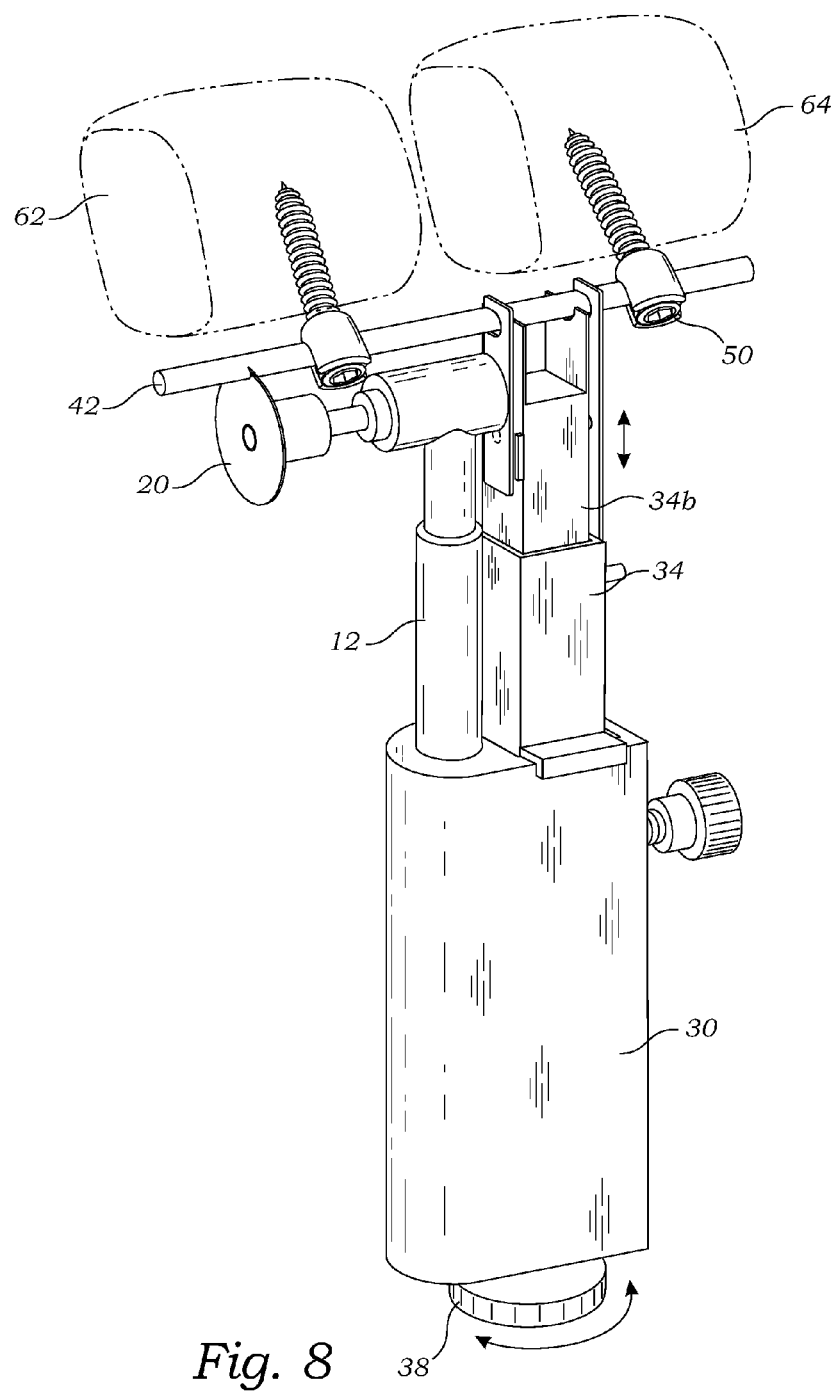
FIG. 8 is a perspective view of the surgical cutting system, according to an alternative embodiment of the present invention.

FIG. 8 is a perspective view of the surgical cutting system 10, according to an alternative embodiment of the present invention. In this embodiment, the guide body 30 has been extended to form a housing or shield around the rod cutting tool 12. It also saves time by avoiding the step of assembling the rod cutting tool 12 with the guide device 14. In FIG. 8 the guide body 30 is shown with a rounded surface, however any shape, square, hexagonal, etc., which has the similar effect of enclosing the rod cutting tool 12, is considered equivalent and within the scope of the present invention. The actuation of the adjustment mechanism 38 and the resulting linear motion of the distal end 34 are shown as the cutting element 20 begins a cut into the rod 42.

FIGS. 9 and 10 are perspective views of the surgical cutting system 10, according to an alternative embodiment of the present invention. In this embodiment, the housing 16 of the rod cutting tool 12 is able to be substantially inserted into the elongate body 34. The cutting shaft 26 and the cutting element 20 remain exposed within the distal end 34b of the elongate body 34. The guide body 30 (shown in FIG. 8) is also fully within the elongate body 34. The rod cutting tool 12 is then approximately centered within the distal end 34b of the elongate body 34, with the C-shaped receivers 44 on either side of the rod cutting tool 12. The mechanism for aligning the rod cutting tool 12 along the rod 42 using the lateral adjustment screw 36 is also enclosed fully within the elongate body 34, but essentially retains the same functionality as described above. A stop 49, in this case the shape of a rectangular tap connected to the elongate body 34, is for stopping the rotational motion of the movable arm 46 about the pin 48. The stop 49 is located to allow the movable arm 46 to fully disengage from the C-shaped receiver 44 to allow release or capture of the rod 42. FIG. 10 shows the rod cutting tool 12 within the elongate body 34.

Figure 11:
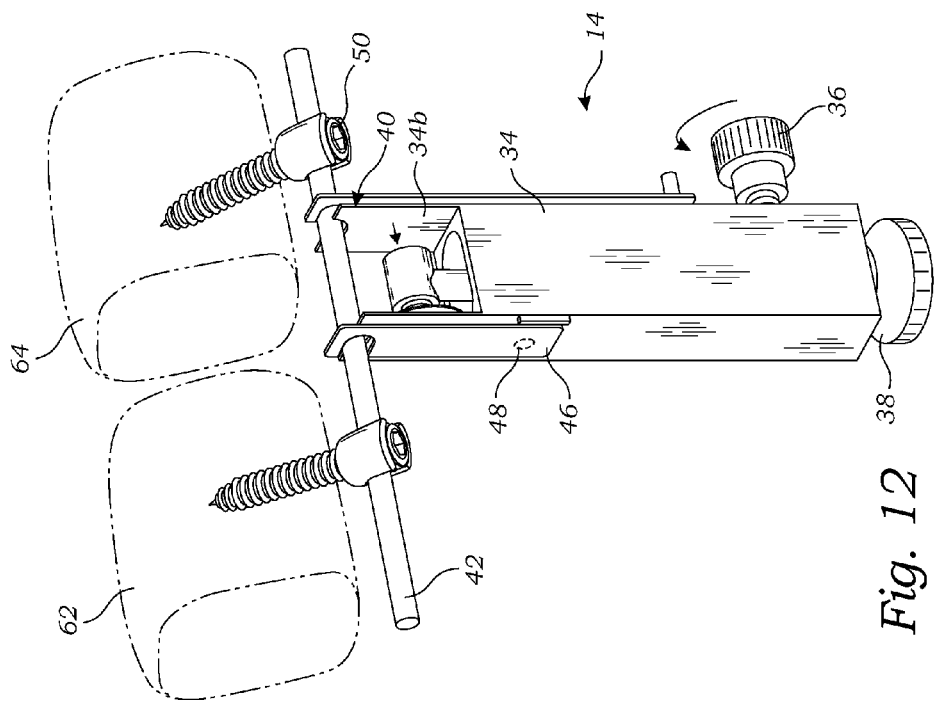
FIGS. 11, 12, and 13 are perspective views illustrating the operation of the surgical cutting system as described in the embodiment shown in FIGS. 9 and 10.
Figure 12:
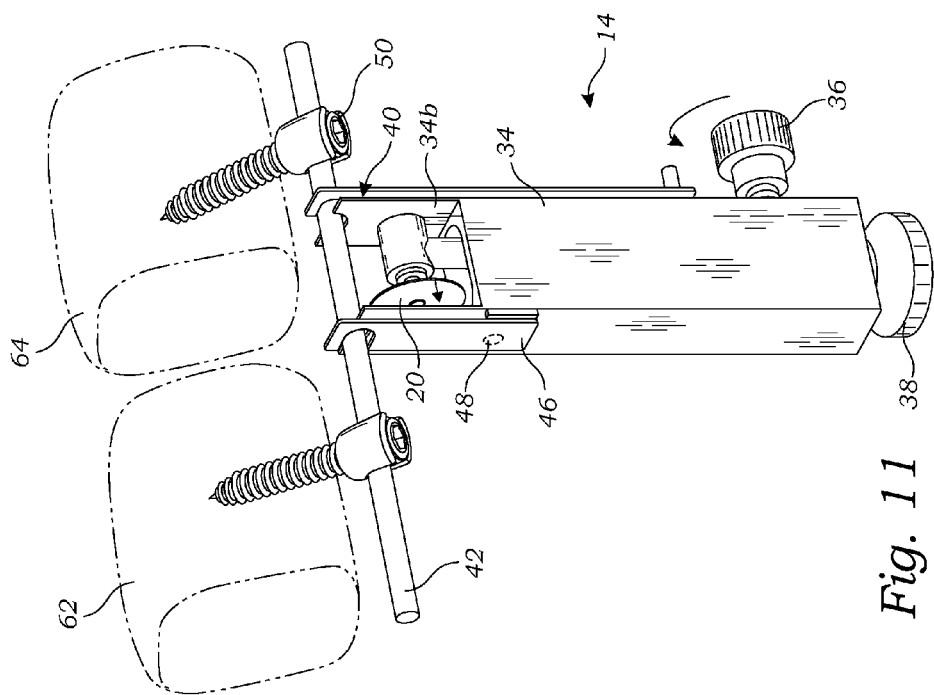
Figure 13:
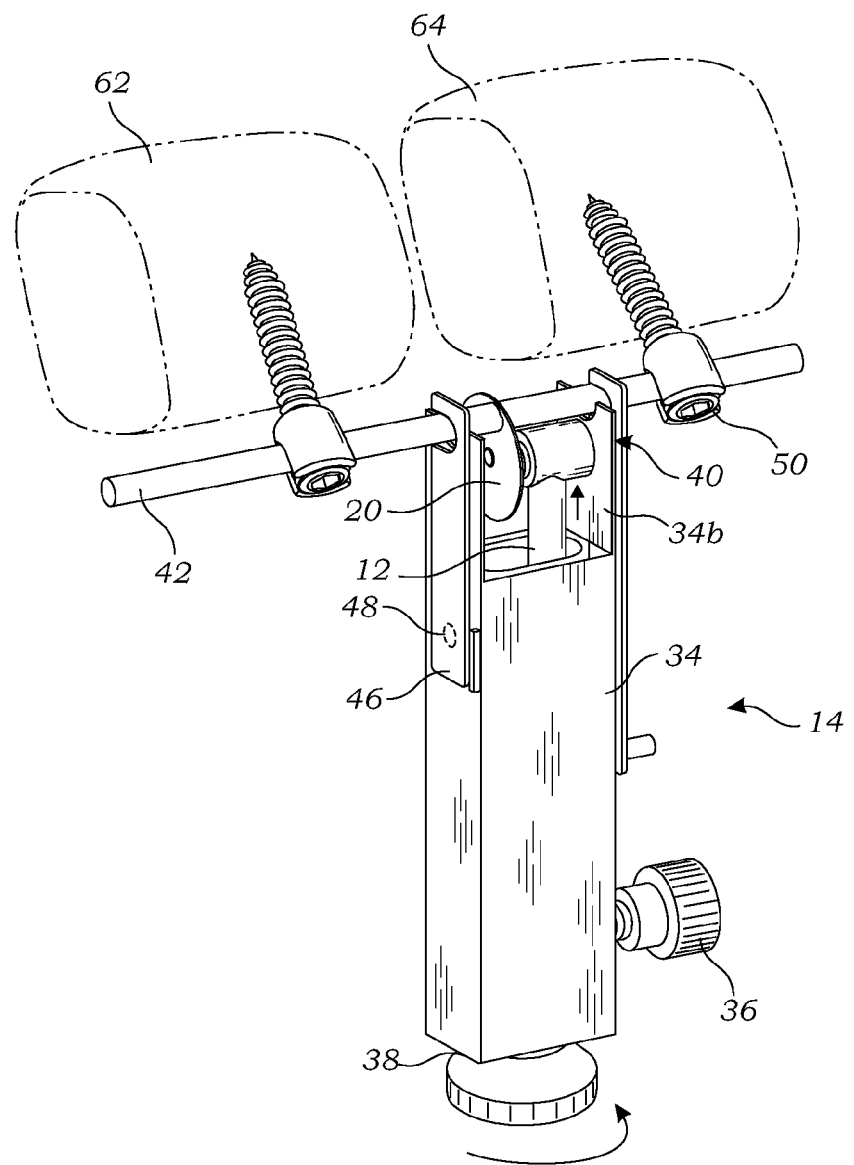

FIGS. 11, 12, and 13 are perspective views of the surgical cutting system 10, as described in the embodiment shown in FIGS. 9 and 10, illustrating the operation of the surgical cutting system 10. FIG. 11 shows the surgical cutting system 10 clamped to a rod 42. Here the lateral adjustment screw 36 is operated to begin the lateral motion of the cutting element 20 along the rod 42. FIG. 12 shows a continuation of the lateral motion where the cutting element 20 has reached the desired position along the rod 42. FIG. 13 shows the adjustment mechanism 38 operated to actuate the rod cutting tool 12 towards the rod 42 and perform the cut.

Figure 14:
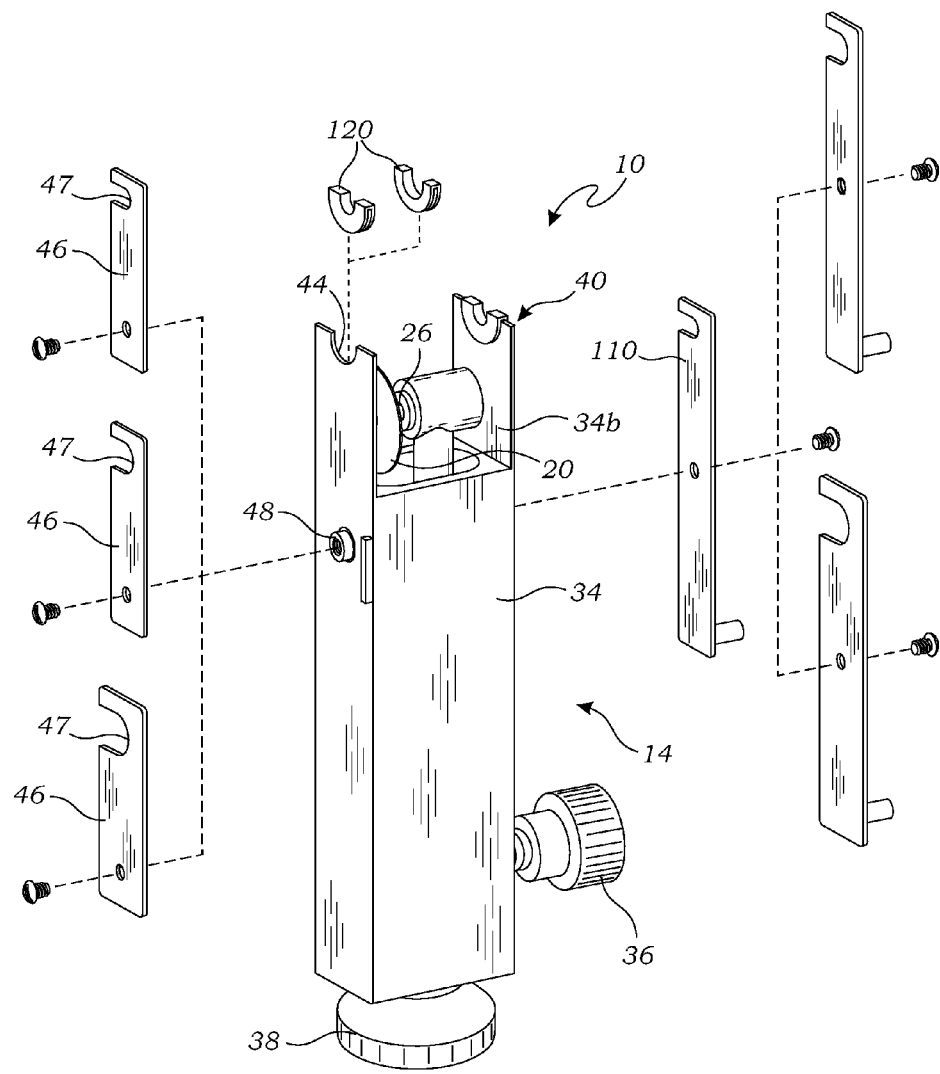
FIG. 14 is a perspective view of the surgical cutting system of the embodiment of FIG. 9, illustrating alternate shapes of the recessed portion of the movable arm.

FIG. 14 is a perspective view of the surgical cutting system 10, illustrating multiple embodiments of the movable arm 46 that each include an alternative shape of the recessed portion 47. The movable arms 46 are shown to be interchangeable to select the recessed portion 47 which will provide a firm clamp around rods 42 of varying diameter. Each movable arm 46 is designed to be connected to the elongate body 34 by the pin 48 (or alternative connection mechanism). The shape of the recessed portion 47 is generally shaped to abut the rod 42, with one end rounded; however other recesses may be rectangular, hexagonal, may also be used, and should be considered within the scope of the present invention.

The surgical cutting system 10 may be made from any appropriate material that is well known within the art, such as hardened stainless steel or hardened tool steel or the like. The material used should be biologically acceptable to be used inside the patient's body without producing any unwanted effects.

Figure 15:
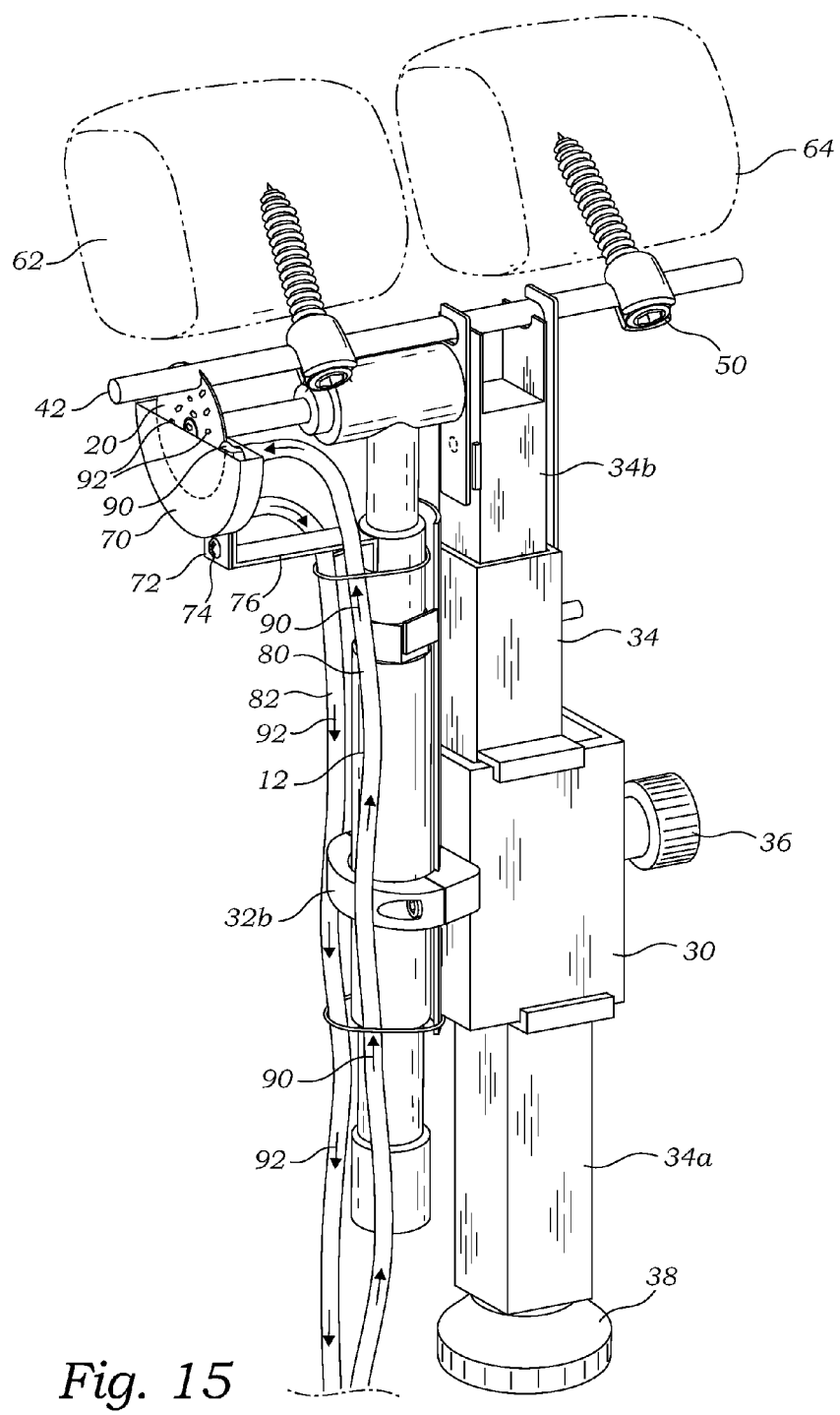
FIG. 15 is a perspective view of the surgical cutting system of FIG. 1, with the inclusion of a blade guard, a first tube, and a second tube.
Figure 16:
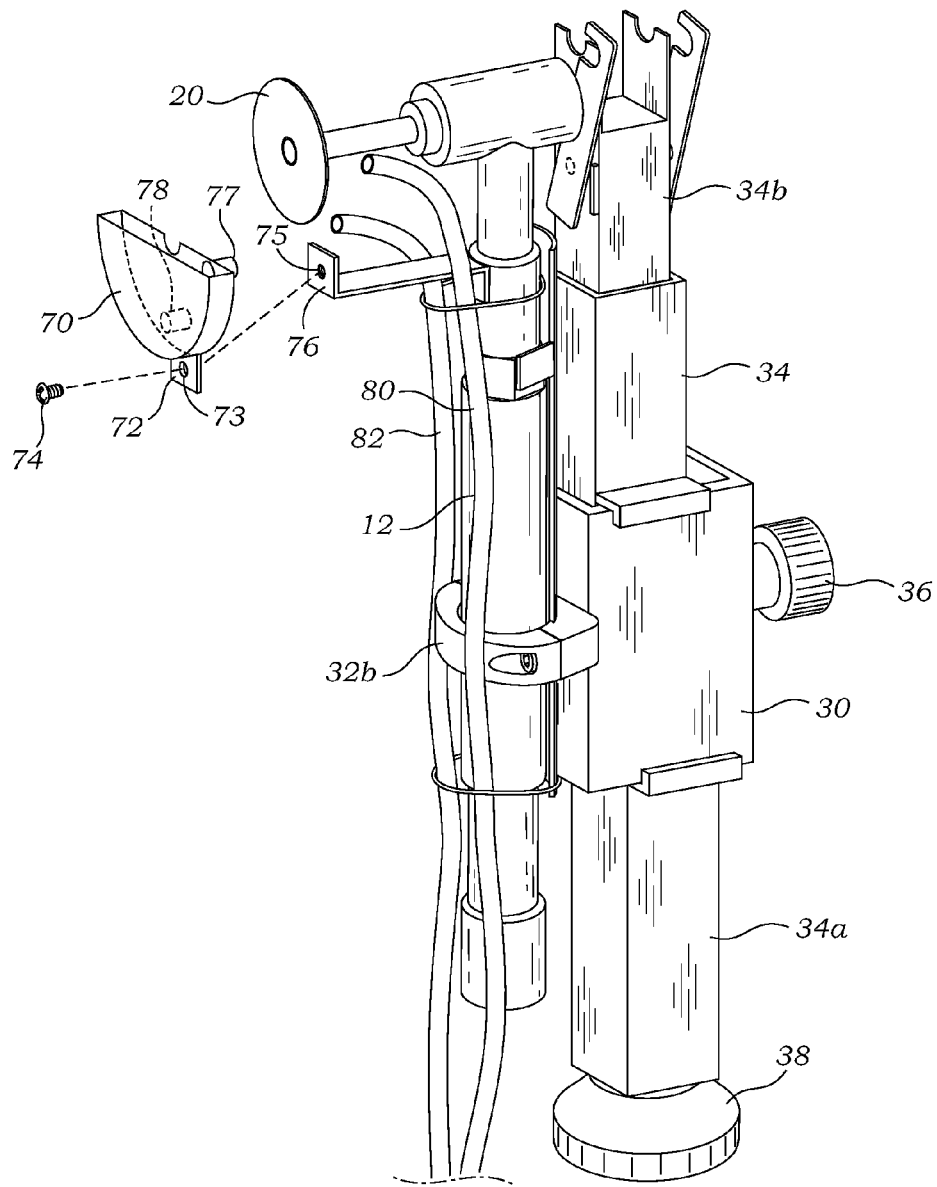
FIG. 16 is an exploded perspective view of the surgical cutting system of the embodiment of FIG. 15.

FIG. 15 is a perspective view of the surgical cutting system 10 of FIG. 1, with the inclusion of a blade guard 70, a mounting bracket 76, a first tube 80, and a second tube 82. FIG. 16 is an exploded perspective view of the surgical cutting system 10 of the embodiment of FIG. 15. In the present embodiment, the blade guard 70 is made of two circular segments connected at their curved edges by a narrow wall, though in other embodiments alternate designs for the shape of the blade guard 70 may be used. When the blade guard 70 is in place, the cutting element 20 may reside, in part, within the space inside the blade guard 70. This is to protect the user from flying debris caused by cutting or from material introduced through either the first tube 80 or the second tube 82. The blade guard 70 also has a first port 77 and a second port 78, which, in the present embodiment, are short hollow tubes affixed to the blade guard 70 to allow the passage of material to/from the first port 77 and the second port 78 into/out of the area within the blade guard 70 and proximate to the cutting element 20. In the present embodiment, the first tube 80 may be used to inject an inflow 90 of material, where the inflow 90 may be water, saline, air, or any composition of matter needed according to those skilled in the art. Also, in the present embodiment, the second tube 82 may be used to extract an outflow 92 of material from the region around cutting element 20, where the outflow 92 may be water, saline, blood, metal shavings, bone shards, a mixture of those, etc. The directionality of the flow through the first tube 80 and the second tube 82 is arbitrary and may be reversed or identical. The first port 77 may be connected to the first tube 80 by stretching the end of the flexible first tube 80 over the first port 77. Similarly, the second port 78 may be connected to the second tube 82 by stretching the end of the flexible second tube 82 over the second port 78, though other methods of attachment of each are possible. Also, the first tube 80 and the second tube 82 may be fastened to the rod cutting tool 12 at a number of locations using thin wires, wire ties, cable, etc. to keep the tubes out of the way of the user and to reduce tension at their connection points to the blade guard 70.

As shown in FIGS. 15-16, the blade guard 70 has a mounting flange 72, which may be a planar extension off the blade guard 70, coplanar with the cutting element 20, and may be used to attach the blade guard 70 to the rod cutting tool 12 via the mounting bracket 76. The mounting bracket 76, when connected, allows the blade guard 70 to be positioned at the proper lateral distance from the rod cutting tool 12 to cover a portion of the cutting element 20. The mounting bracket 76 may be attached to the rod cutting tool 12 by any method known to those skilled in the art, including welding, tack welding, soldering, adhesives, etc. The mounting bracket 76 may be S-shaped, as shown in FIGS. 15-16, or may be any other shape known to those skilled in the art that would allow mounting to the blade guard 70 and the rod cutting tool 12. In the present embodiment, the mounting flange 72 has an aperture 73 and the mounting bracket 76 has a threaded hole 75. A fastener 74 may then be inserted through the aperture 73 to engage the threaded hole 75 and fasten the blade guard 70 to the mounting bracket 76. While FIGS. 15-16 illustrate one embodiment of the blade guard 70 and the mounting bracket 76, other embodiments may be derived by those skilled in the art, with such variations being considered equivalent and within the scope of the present invention.

As illustrated in FIGS. 1-16, the surgical cutting system 10 of the present invention may be used not only to trim the rod 42, but can also be used when removing the hardware such as the pedicle screw 50 from the patient's body. Sometimes the locking nut 58 gets stripped, and if the rod 42 can be cut inside the patient's body, the pedicle screw 50 can be removed without disconnecting the rod 42. The rod 42 can simply be cut and then unscrew the pedicle screw 50 with the portion of rod 42 still attached.

The invention also includes a method of using the surgical cutting system 10, as described above, for cutting a rod as part of spinal fusion surgery. In this method, first the rod cutting tool 12 is brought in alignment with the curved receiver element 32a such that the facets 28 are also aligned with the locking walls 33. Once properly aligned the C-clamp 32b may be tightened to firmly attach the rod cutting tool 12 with the guide body 30.

Next the rod clamping element 40 may be brought into action by first aligning the rod 42 with the C-shaped receivers 44 and the movable arm 46 is turned to lock the rod 42. Now when the system 10 is assembled the power source 22 may be activated to start the drive motor 18. Now when the cutting element 20 is operating the adjustment mechanism 38 may be rotated to move the guide body 30 along the elongate body 34 to bring the cutting element 20 to cut the rod 42.

After the cutting of the rod 42 the adjustment mechanism 38 may be rotated in another direction to move the cutting element 20 away from the rod.

Although a particular exemplary embodiment of the invention has been disclosed in detail for illustrative purposes, it will be recognized to those skilled in the art that variations or modifications of the disclosed invention, including the rearrangement in the configurations of the parts, changes in sizes and dimensions, variances in terms of shape may be possible. Accordingly, the invention is intended to embrace all such alternatives, modifications and variations as may fall within the spirit and scope of the present invention.

The exemplary embodiments described herein detail for illustrative purposes are subject to many variations of structure and design. It should be emphasized, however that the present invention is not limited to the particular surgical cutting system 10 as shown and described. Rather, the principles of the present invention can be used with a variety of configurations and arrangements of surgical cutting systems. In particular, the surgical cutting system 10 may be used to cut a rod on any part of the body, including arms, legs, fingers, etc. It is understood that various omissions, substitutions of equivalents are contemplated as circumstances may suggest or render expedient, but the present invention is intended to cover the application or implementation without departing from the spirit or scope of the claims.

As used in this application, the words "a," "an," and "one" are defined to include one or more of the referenced item unless specifically stated otherwise. Also, the terms "have," "include," "contain," and similar terms are defined to mean "comprising" unless specifically stated otherwise. Furthermore, the terminology used in the specification provided above is hereby defined to include similar and/or equivalent terms, and/or alternative embodiments that would be considered obvious to one skilled in the art given the teachings of the present patent application.

What is claimed is:

1. A surgical cutting system for cutting a rod as part of spinal fusion surgery, the surgical cutting system comprising:
a rod cutting toot comprising:
a housing containing a drive motor; and
a cutting element operably mounted on the housing and operably connected with the drive motor;
a guide device comprising:
a guide body;
an attachment mechanism for attaching the rod cutting tool to the guide body;
an elongate body that extends from a proximal end to a distal end, the elongate body being movably mounted on the guide body for moving between an extended position and a retracted position;
a rod-clamping element operably mounted on and/or formed by the distal end of the elongate body, the rod-clamping element being shaped to lockingly engage the rod during the spinal fusion surgery when the elongate body is in the extended position, and position the cutting element adjacent the rod; and
an adjustment mechanism for moving the elongate body relative to the guide body from the extended position to the retracted position, thereby moving the cutting element to cut the rod; and
further comprising a blade guard having a mounting flange, the blade guard operably attached to a mounting bracket which is also attached to the rod cutting tool.

2. The surgical cutting system of claim 1, wherein the cutting tool is a rotary cutting tool, and the cutting element is a cutting disk.

3. The surgical cutting system of claim 1, wherein the guide body is a tubular body having a generally rectangular cross section, and the elongate body has a generally rectangular cross section and is telescopically engaged with the guide body.

4. The surgical cutting system of claim 1, wherein the rod-clamping element includes a generally C-shaped receiver formed in the terminal end of the elongate body, and a movable arm that can move between a locked position and an unlocked position, and which includes a recessed portion that fits around the rod when the movable arm is in the locked position and locks the rod in the C-shaped receiver of the elongate body.

5. The surgical cutting system of claim 1, wherein the adjustment mechanism is a screw mounted on the guide body positioned to move the elongate body between the extended and retracted positions when turned.

6. The surgical cutting system of claim 1, further comprising a lateral adjustment mechanism for moving the rod cutting tool laterally with respect to the rod, for adjusting the location of the cut on the rod.

7. The surgical cutting system of claim 1, wherein the blade guard further includes a first port and a second port, the first port operably connected to a first tube and the second port operably connected to a second tube.

8. A surgical cutting system for cutting a rod, the surgical cutting system comprising:
  a rod cutting tool comprising:
    a housing containing a drive motor, an outer surface of the housing having facets; and
    a cutting element operably mounted on the housing and operably connected with the drive motor;
  a guide device comprising:
    a guide body;
    an attachment mechanism for attaching the rod cutting tool to the guide body;
    a rod engaging body that includes a proximal end to a distal end, the rod engaging body being movably mounted on the guide body for moving between an extended position and a retracted position;
    a rod-clamping element operably mounted on or formed by the distal end of the rod engaging body, the rod-clamping element being shaped to lockingly engage the rod when the rod engaging body is in the extended position, and position the cutting element adjacent the rod; and
    an adjustment mechanism for moving the rod engaging body relative to the guide body from the extended position to the retracted position, thereby moving the cutting element to cut the rod;
  wherein the guide body includes a curved receiver for receiving and engaging the rod cutting tool, the curved receiver including a pair of locking walls that are positioned on either side of the rod cutting tool and which engage the facets of the housing of the rod cutting tool, to prevent rotation of the rod cutting tool while in use; and
  wherein the attachment mechanism includes a C-clamp that fits over the rod cutting tool and is fastened to the guide body with screws to lock the rod cutting tool against the curved receiver.

* * * * *